US007393633B1

(12) United States Patent
Park et al.

(10) Patent No.: US 7,393,633 B1
(45) Date of Patent: Jul. 1, 2008

(54) GENOTYPING KIT FOR DIAGNOSIS OF HUMAN PAPILLOMAVIRUS INFECTION

(75) Inventors: Tae-Shin Park, Seoul (KR); Mi-Sun Park, Seoul (KR); Jeongmi Kim, Seoul (KR)

(73) Assignee: Biomedlab Corporation, Seoul (KR)

( * ) Notice: Subject to any disclaimer, the term of this patent is extended or adjusted under 35 U.S.C. 154(b) by 294 days.

(21) Appl. No.: 09/807,234

(22) PCT Filed: Oct. 26, 2000

(86) PCT No.: PCT/KR00/01213

§ 371 (c)(1), (2), (4) Date: Apr. 6, 2001

(87) PCT Pub. No.: WO01/68915

PCT Pub. Date: Sep. 20, 2001

(30) Foreign Application Priority Data

Mar. 15, 2000 (KR) .............................. 2000-13161

(51) Int. Cl.
*C12Q 1/68* (2006.01)
*C12P 19/34* (2006.01)
*G01N 33/566* (2006.01)
*G01N 30/96* (2006.01)

(52) U.S. Cl. ......................... 435/6; 435/91.1; 435/91.2; 436/501; 422/50; 422/69.1

(58) Field of Classification Search ..................... 435/5, 435/6, 91.1, 91.2; 536/23.1, 23.72, 24.3, 536/24.33; 436/501; 422/50, 69.1
See application file for complete search history.

(56) References Cited

U.S. PATENT DOCUMENTS

| | | | | |
|---|---|---|---|---|
| 5,215,882 | A | 6/1993 | Bahl et al. | |
| 5,273,881 | A * | 12/1993 | Sena et al. | 435/6 |
| 5,484,699 | A | 1/1996 | Bouma et al. | |
| 6,339,147 | B1 * | 1/2002 | Lukhtanov et al. | 536/23.1 |
| 6,352,825 | B1 * | 3/2002 | Meijer et al. | 435/5 |
| 2003/0012695 | A1 * | 1/2003 | Shalon et al. | 422/68.1 |

FOREIGN PATENT DOCUMENTS

| | | | |
|---|---|---|---|
| EP | 0774 518 A2 | | 5/1997 |
| WO | WO 95/22626 | * | 8/1995 |
| WO | WO-98/17829 | | 4/1998 |
| WO | WO-99/14377 | | 3/1999 |

OTHER PUBLICATIONS

Meijer et al. GenEmbl Accession No. A46136.*
Meijer et al. GenEmbl Accession No. A46106.*
Meijer et al. GenEmbl Accession No. A46107.*
Joos et al. Covalent Attachment of Hybridizable Oligonucleotides to Glass Supports, Analytical Biochemistry, 1997, vol. 247, p. 96-101.*
Rogers et al. Immobilization of Oligonucleotides into a glass support via disulfide bonds: a method for preparation of DNA microarrays, Analytical Biochemistry, 1999, vol. 266, p. 23-30.*
Nucleic acid search report Accesson No. U45932.*
Stewart et al. Journal of Virology, 1996, vol. 70(5), p. 3127-3136.*
Buck et al. BioTechniques, 1999, vol. 27(3). p. 528-536.*
Nucleic acid search report Accesson No. U45932, 1996.*
Gravitt et al. (J Clin. Microbiol. (1998) 36(10): 3020-3027).*
Stratagene Catalog (1988).*
Meijer et al. GenEmbl Accession No. A46136, 1997.*
Meijer et al. GenEmbl Accession No. A46106, 1997.*
Meijer et al. GenEmbl Accession No. A46107, 1997.*
Bevan et al. (Biochem J. (1990) 267(1): 119-123).*
Zamatteo et al. (Analytical Biochemistry (2000) 280:143-150).*
Barbany et al., "Molecular genetic applications of streptavidin-coated manifold supports," Biomolecular Engineering 1999;16:105-111.

* cited by examiner

*Primary Examiner*—Kenneth R. Horlick
*Assistant Examiner*—Joyce Tung
(74) *Attorney, Agent, or Firm*—Darby & Darby PC

(57) ABSTRACT

The present invention relates to a genotyping kit for diagnosing patients infected with human papillomavirus (HPV), and a method for diagnosis of HPV infection by genotyping specimen DNA isolated from the patients using the said kit. The genotyping kit of the invention comprises a DNA chip with probes that have nucleotide sequences complementary to DNA of HPV, primers for amplifying the DNA of a sample by PCR, and means for labeling hybridized sample DNA with the DNA chip. The method for diagnosis of HPV infection comprises the steps of amplifying DNA obtained from a sample using the primers of the kit, applying the amplified DNA to the DNA chip and hybridizing the amplified DNA and the probes of the DNA chip, and detecting DNA bound on the surface of the DNA chip by labeling hybridized DNA. In accordance with the invention, the genotyping kit may be practically applied to the early diagnosis, prevention and treatment of cervical cancer, since the kit can easily diagnose HPV infection, and can exactly determine the genotype of the HPV.

2 Claims, 16 Drawing Sheets

GENOTYPING KIT FOR DIAGNOSIS OF HUMAN PAPILLOMAVIRUS INFECTION

BACKGROUND OF THE INVENTION

1. Field of the Invention

The present invention relates to a genotyping kit for diagnosis of human papillomavirus (HPV) infection, more specifically, to a genotyping kit for detecting human papillomaviruses from clinical samples of infected patients using a DNA chip, and a process for preparing the said DNA chip and a method for diagnosis of HPV infection using the said genotyping kit.

2. Background of the Invention

Uterine cancer includes cervical cancer, endometrial cancer, uterine sarcoma and the like. For cervical cancer, approximately 450,000 new cases occur worldwide each year and approximately 6,000 in Korea. Since the occurrence of cervical cancer (including cervical intraepithelial neoplasia) occupies 22.1% of total cancer cases in Korean women, the highest incidence with the second highest death rate, the prevention, diagnosis and treatment of cervical cancer are regarded as the most important issue in women's health.

Cervical cancer progresses through a precancerous stage, cervical intraepithelial neoplasia (CIN) known to be mainly caused by human papillomavirus (HPV) infection. Especially, infection by particular types of HPV raises the possibility of developing invasive disease. Over 70 genotypes of HPV have been identified since the recognition of HPV as the main etiological factor for cervical cancer. Certain HPV genotypes were selectively found in the lesions of specific location or progression stage, which rendered the biological diversity of HPV infection realized. Among the HPV genotypes detected in the anogenital area, over 10 genotypes have been classified as the high-risk group that are associated with an elevated risk for developing cervical cancer. Based on these findings, characterization of the biological differences of HPV infection is considered to be of significant importance to the diagnosis and prevention of cervical cancer.

For the diagnosis of cervical cancer at its early stage, Pap smear test has been most commonly used which is a cytological test performed as follows: old cells removed from the outermost layer of cells from the surface of the cervix are stained and examined for histopathological characteristics of HPV infection including koilocytosis, formation of perinuclear halo in the epithelial cells. However, due to the low diagnostic efficiency (1-15%) of Pap test together with other limitations, additional methods such as colposcopy are necessary for more dependable diagnosis. Colposcopic screening can detect HPV infection up to 70% but has disadvantages including high cost of the equipment, the need for skilled interpreters, and incapability of determining HPV genotypes to distinguish between the high-risk and low-risk infection. Therefore, efforts have been made continuously to develop techniques for the detection of HPV and identification of HPV genotypes to supplement conventional screening methods for cervical cancer and its precursors including Pap test.

The methods for detection of HPV and identification of HPV genotypes can be classified into two groups, i.e., direct detection of HPV DNA and detection of amplified HPV DNA. The methods for direct detection of HPV DNA include liquid hybridization (HYBRID CAPTURE® kit by Digene Diagnostics, Silver Spring, Md., USA), Southern blot and dot blot with HPV type-specific probes, filter in situ hybridization (FISH) and the like, and the methods for the detection of amplified DNA include type-specific PCR (polymerase chain reaction) and general-primer PCR. In particular, genotype analyses of amplified HPV DNA by general primer sets are commonly performed by employing dot blot hybridization, microtiter plate hybridization, or line probe assay. Among these methods, liquid hybridization by HYBRID CAPTURE® and line probe assay following general-primer PCR have been considered most suitable for diagnostic purposes. The line probe assay can detect about 20 different HPV genotypes by immobilized oligonucleotide probes on a nitrocellulose membrane, however, it lacks reliability due to low sensitivity and difficulties in data interpretation. Commercialized HYBRID CAPTURE® kit can detect HPV DNA in clinical samples without PCR amplification and distinguish between high-risk and low-risk HPV groups. However, the fact that HYBRID CAPTURE® kit cannot identify the genotypes of infecting HPV limits accurate risk determination since the risk factor amongst the high-risk HPV is not the same, in other words, intermediate-risk types are included in the high-risk group Moreover, the use of RNA probe may pose low stability of the kit, and also possibility of contamination cannot be excluded.

Under these circumstances, there have been strong reasons for exploring and developing a simple and accurate method for detection of HPV infection and identification of the genotype of infecting HPV.

SUMMARY OF THE INVENTION

The present inventors have tried to detect HPV infection and identify the types of HPV by way of genotyping DNA from clinical samples and prepared an HPV genotyping kit comprising a DNA chip with probes that have nucleotide sequences complementary to the DNA of HPV, primers for amplifying DNA obtained from clinical samples by PCR, and means for labeling amplified DNA hybridized to the probes of the said DNA chip, and successfully detected HPV infection and identified genotypes of infecting HPV by the aid of the genotyping kit in a simple and accurate manner.

A primary object of the present invention is, therefore, to provide a genotyping kit for diagnosis of HPV infection.

The other object of the invention is to provide a process for preparing the DNA chip contained in the HPV genotyping kit.

Another object of the invention is to provide a method for diagnosis of HPV infection using the HPV genotyping kit.

BRIEF DESCRIPTION OF THE DRAWINGS

The above and the other objects and features of the present invention will become apparent from the following description given in the conjunction with the accompanying drawings, in which.

FIG. **2*a*** is a photograph showing the result of HPV 16 DNA analysis.

FIG. **2*b*** is a photograph showing the result of HPV 18 DNA analysis.

FIG. **2*c*** is a photograph showing the result of HPV 31 DNA analysis.

FIG. **2*d*** is a photograph showing the result of HPV 33 DNA analysis.

FIG. **2*e*** is a photograph showing the result of HPV 35 DNA analysis.

FIG. **2*f*** is a photograph showing the result of HPV 39 DNA analysis.

FIG. **2*g*** is a photograph showing the result of HPV 45 DNA analysis.

Figure 2A:
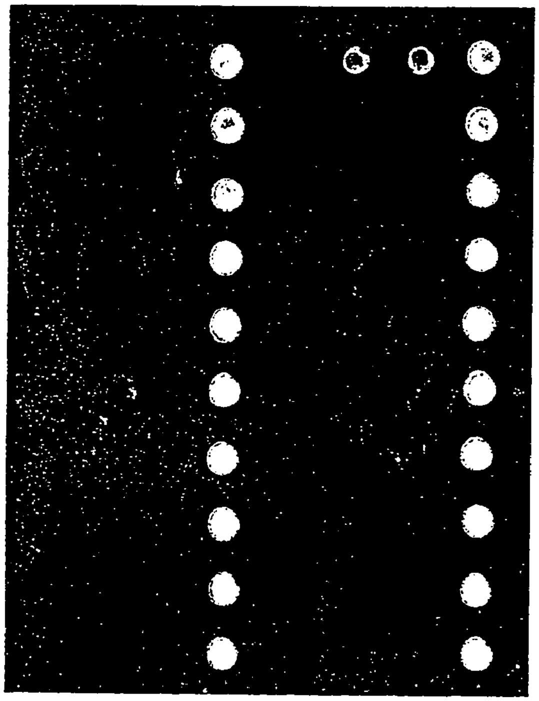
Figure 2B:
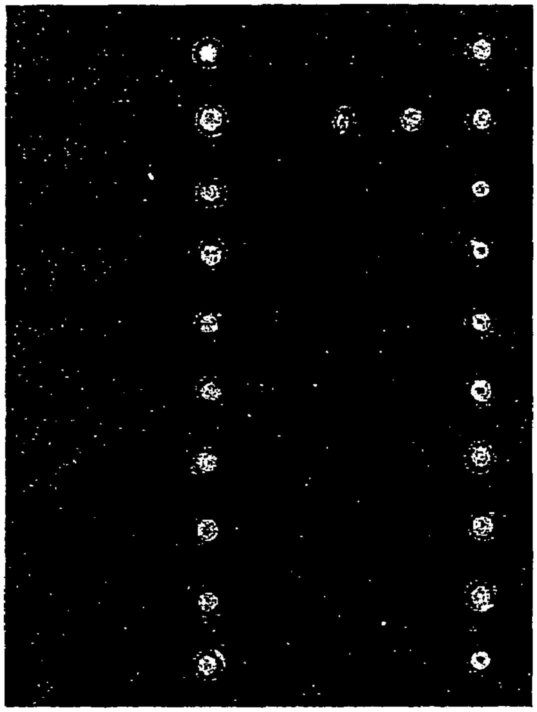
Figure 2C:
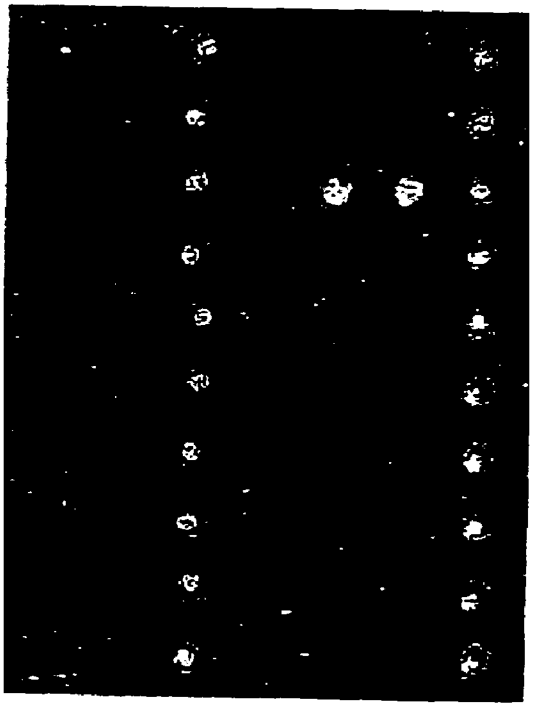
Figure 2D:
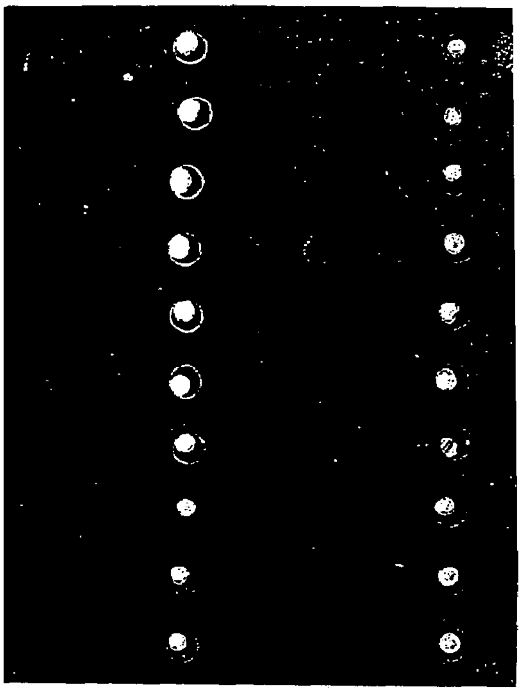
Figure 2E:
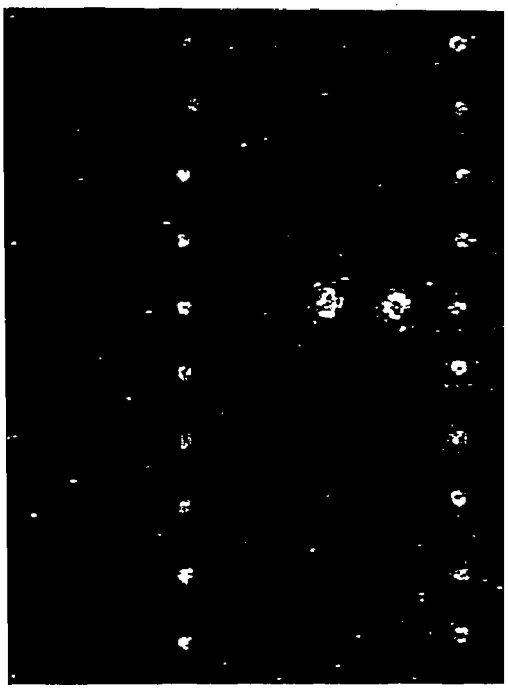
Figure 2F:
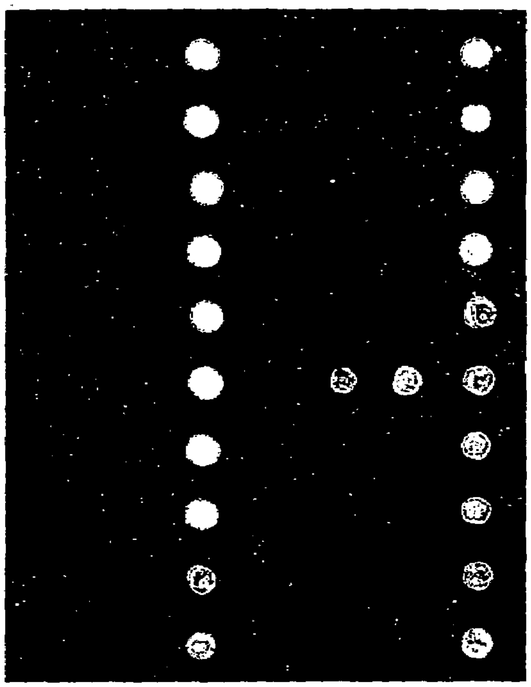
Figure 2G:
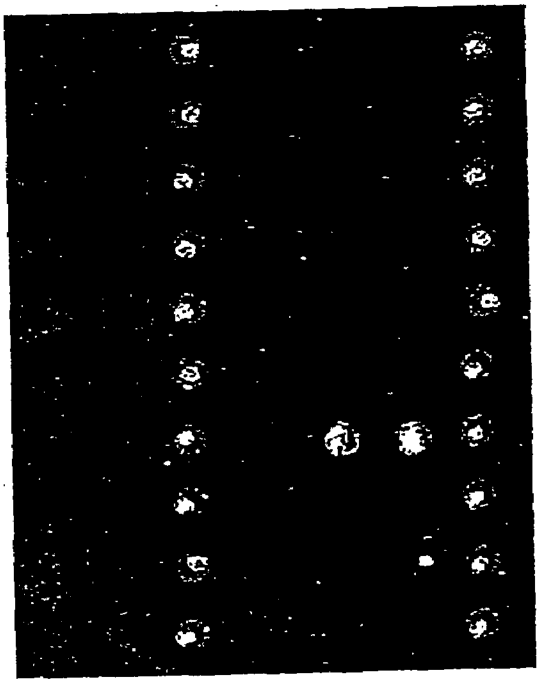
Figure 2H:
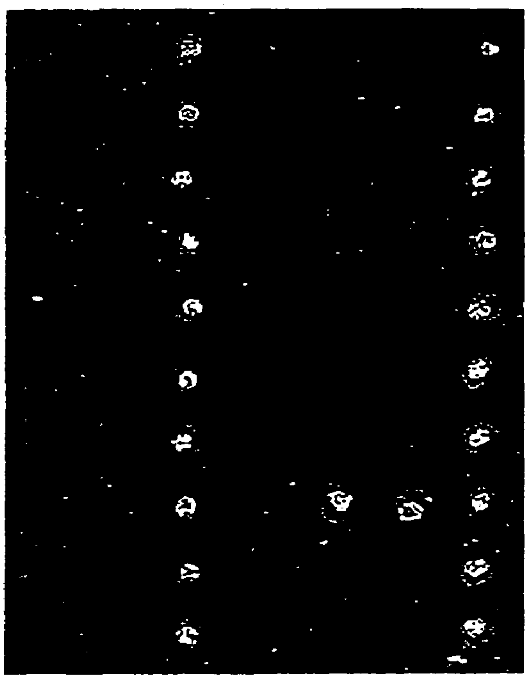

FIG. 2*h* is a photograph showing the result of HPV 51 DNA analysis.

Figure 2I:
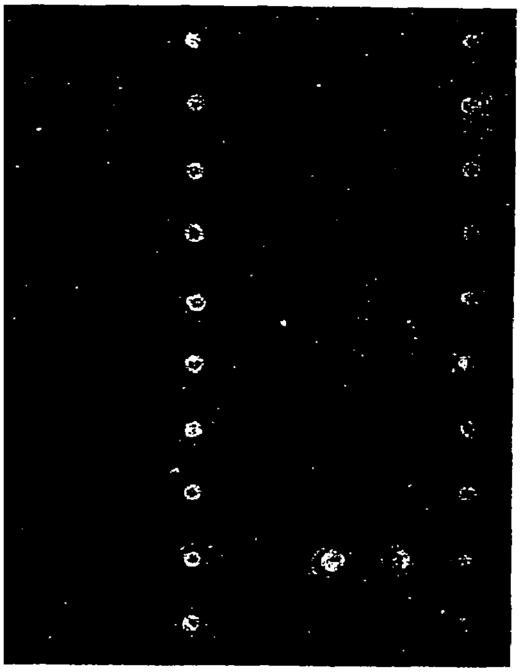

FIG. 2*i* is a photograph showing the result of HPV 52 DNA analysis.

Figure 2J:
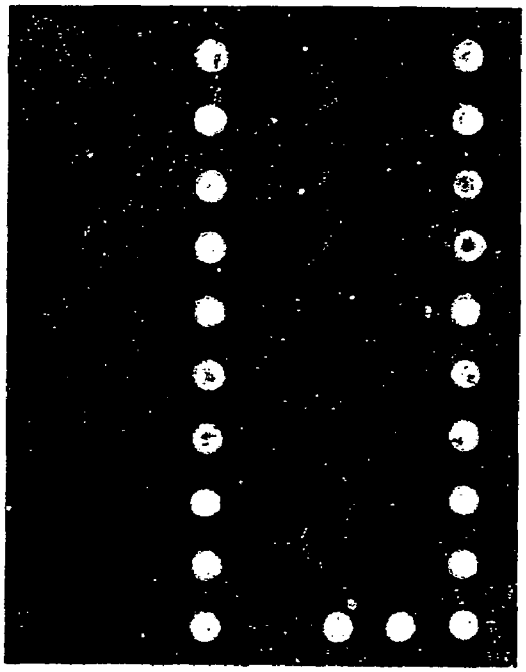

FIG. 2*j* is a photograph showing the result of HPV 56 DNA analysis.

Figure 2K:
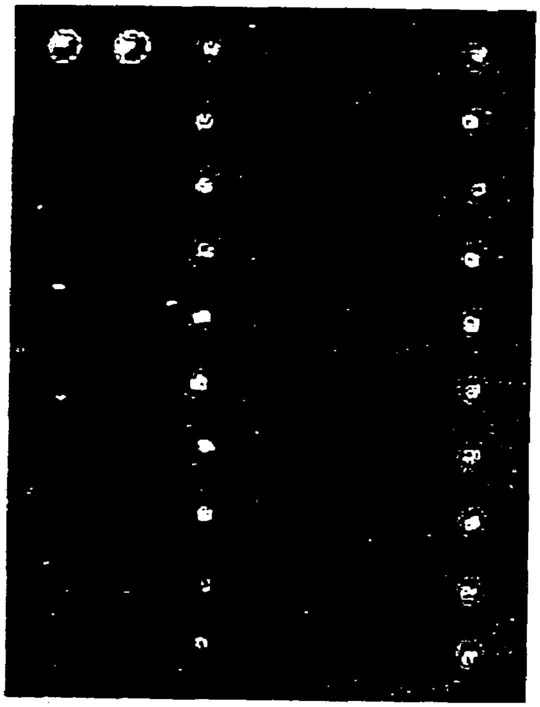
Figure 2L:
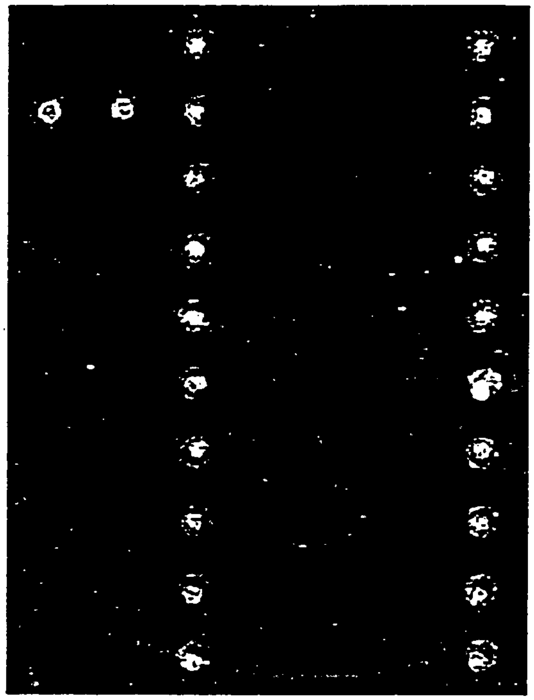

FIG. 2*k* is a photograph showing the result of HPV 58 DNA analysis.

FIG. 21 is a photograph showing the result of HPV 59 DNA analysis.

Figure 2M:
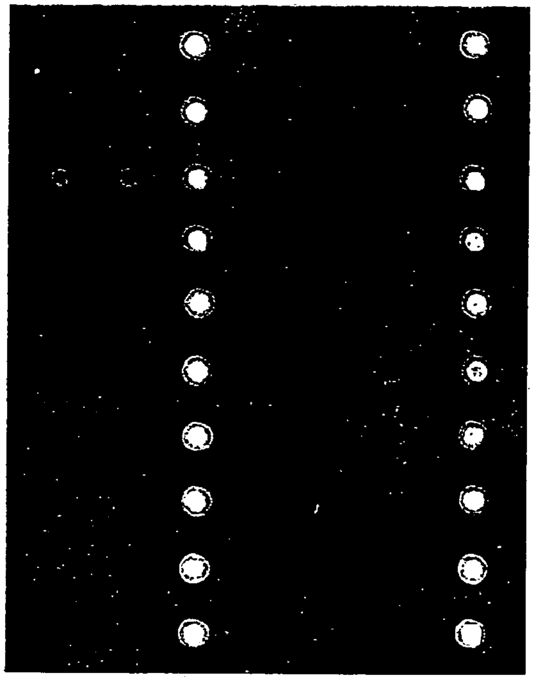

FIG. 2*m* is a photograph showing the result of HPV 66 DNA analysis.

Figure 3A:
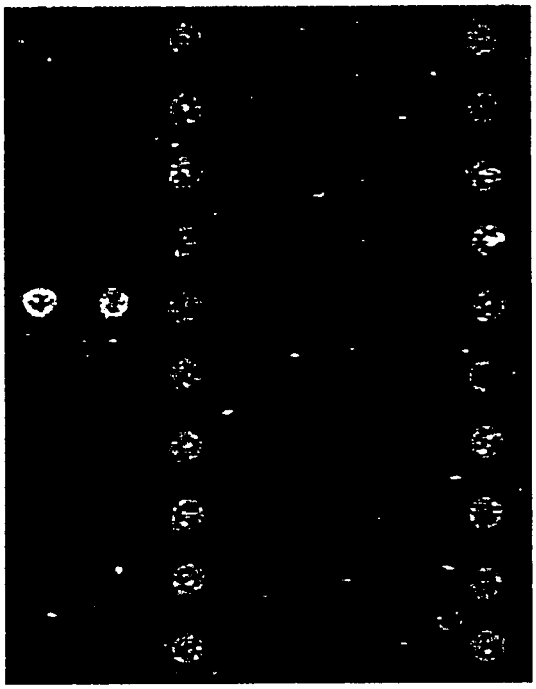

FIG. 3*a* is a photograph showing the result of HPV 6 DNA analysis.

Figure 3B:
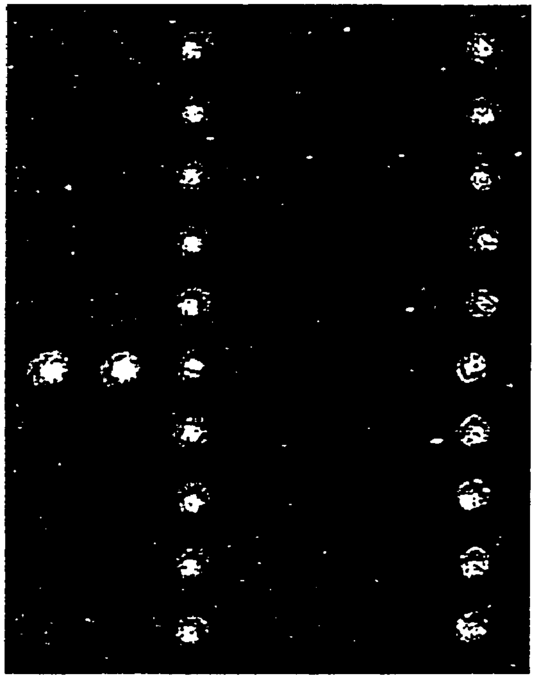

FIG. 3*b* is a photograph showing the result of HPV 11 DNA analysis.

Figure 3C:
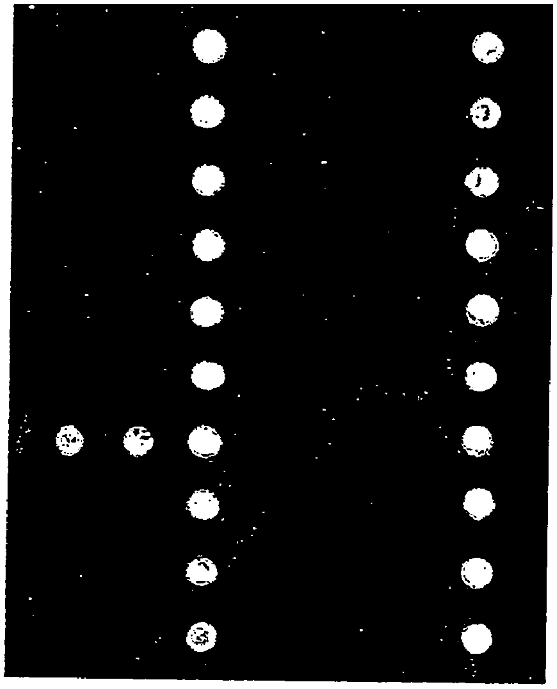

FIG. 3*c* is a photograph showing the result of HPV 34 DNA analysis.

Figure 3D:
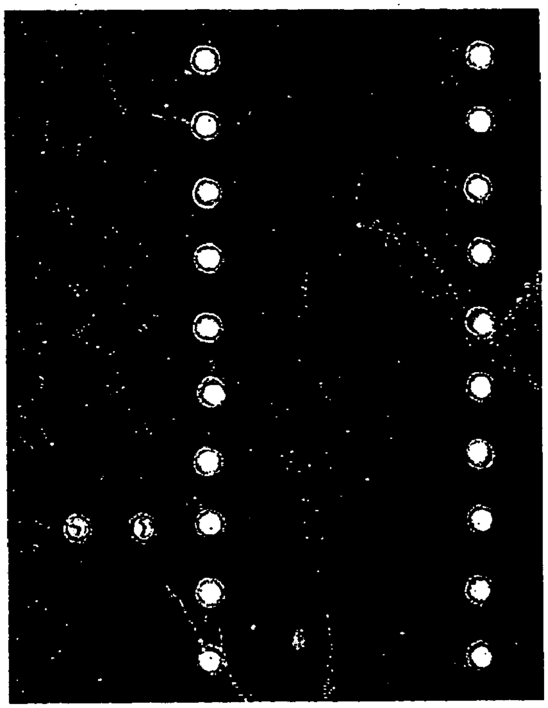

FIG. 3*d* is a photograph showing the result of HPV 40 DNA analysis.

Figure 3E:
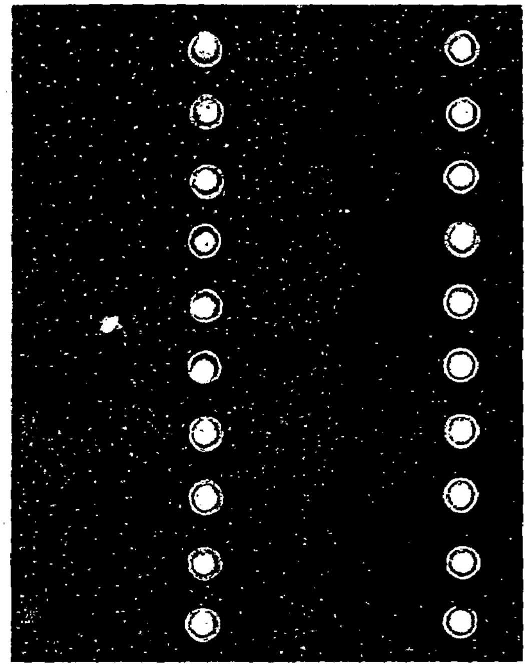

FIG. 3*e* is a photograph showing the result of HPV 42 DNA analysis.

Figure 3F:
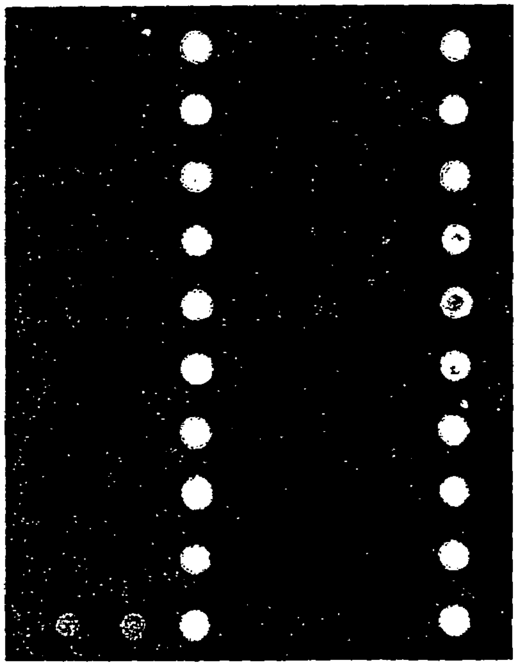

FIG. 3*f* is a photograph showing the result of HPV 44 DNA analysis.

Figure 4A:
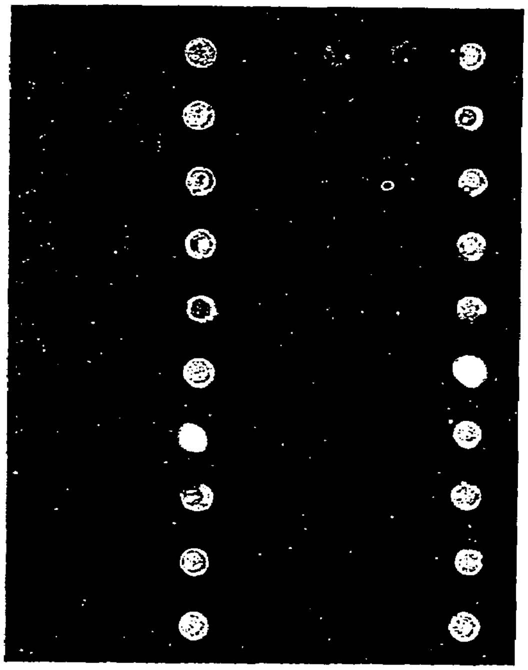

FIG. 4*a* is a photograph showing the result of DNA analysis of sample number 43 using the DNA chip of the invention.

Figure 4B:
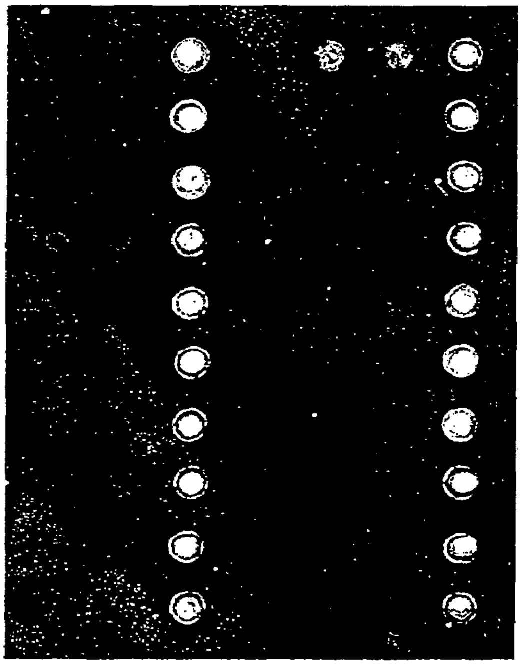

FIG. 4*b* is a photograph showing the result of DNA analysis of sample number 46 using the DNA chip of the invention.

Figure 4C:
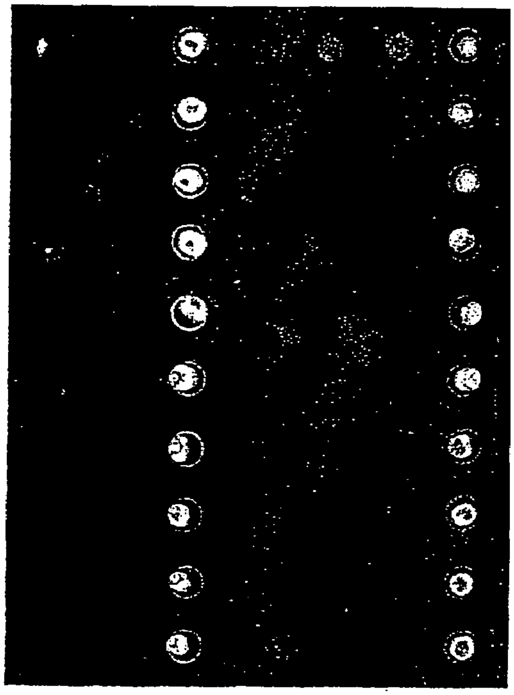

FIG. 4*c* is a photograph showing the result of DNA analysis of sample number 47 using the DNA chip of the invention.

Figure 4D:
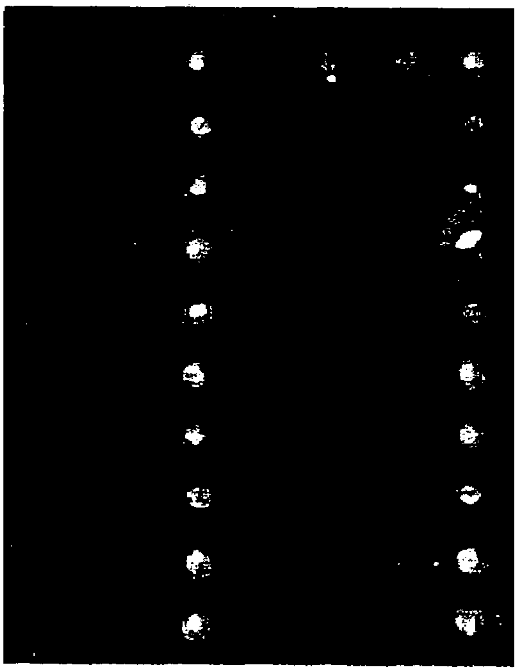

FIG. 4*d* is a photograph showing the result of DNA analysis of sample number 51 using the DNA chip of the invention.

Figure 4E:
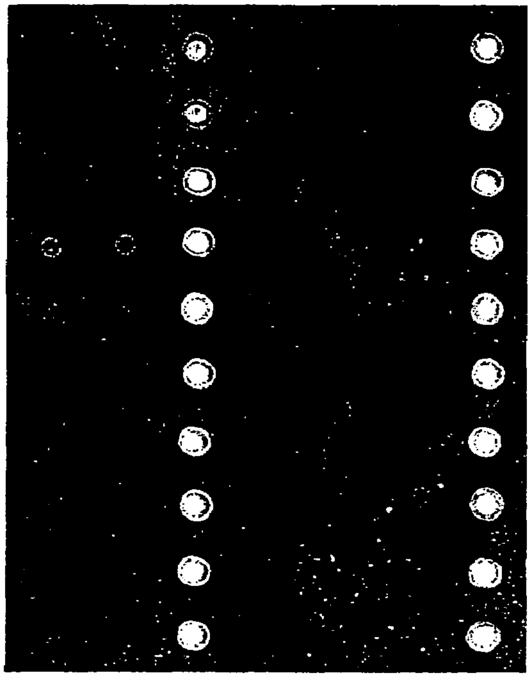

FIG. 4*e* is a photograph showing the result of DNA analysis of sample number 52 using the DNA chip of the invention.

Figure 4F:
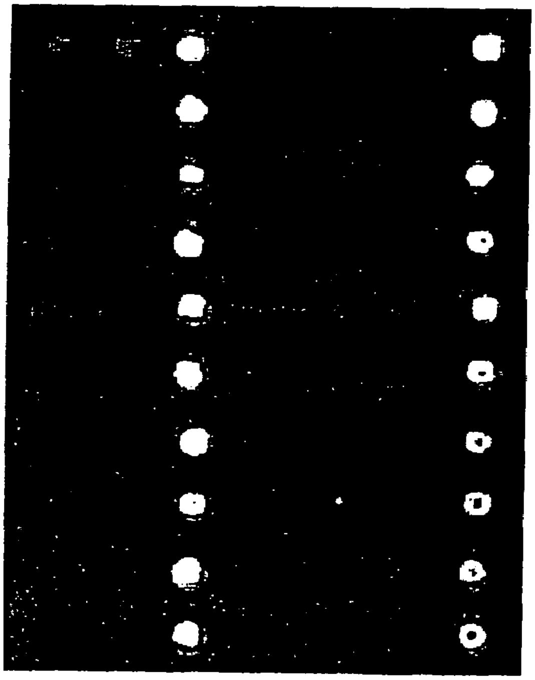

FIG. 4*f* is a photograph showing the result of DNA analysis of sample number 53 using the DNA chip of the invention.

Figure 4G:
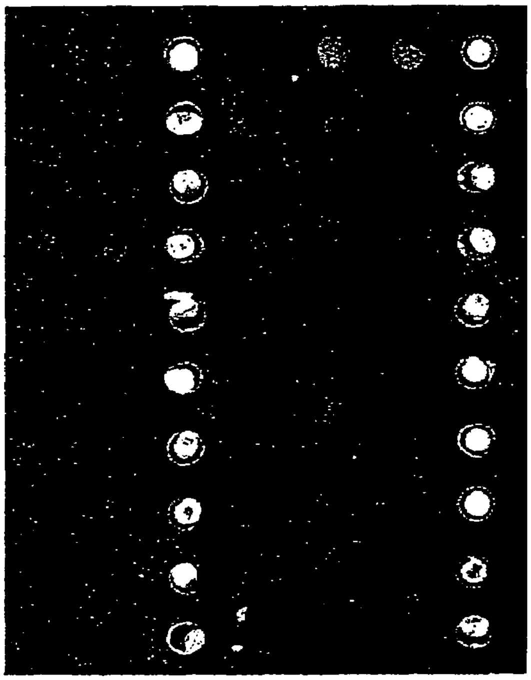

FIG. 4*g* is a photograph showing the result of DNA analysis of sample number 54 using the DNA chip of the invention.

Figure 4H:
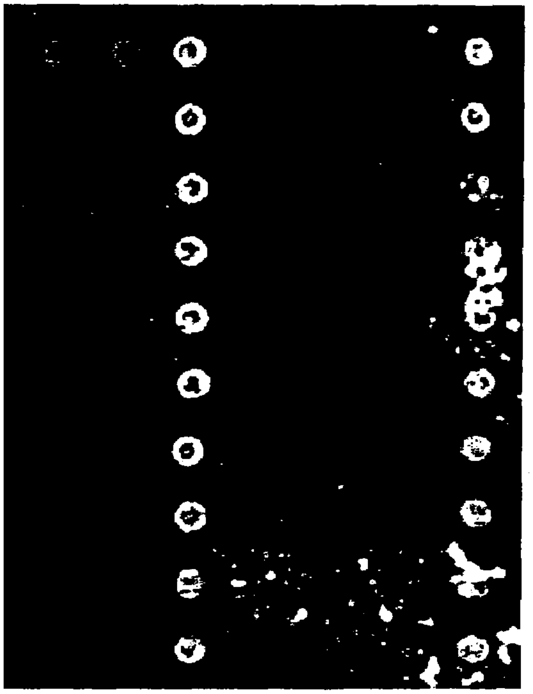

FIG. 4*h* is a photograph showing the result of DNA analysis of sample number 57 using the DNA chip of the invention.

Figure 4I:
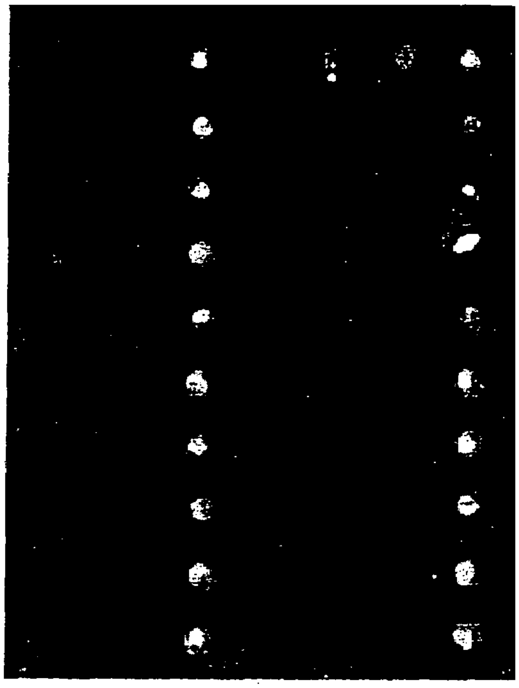

FIG. 4*i* is a photograph showing the result of DNA analysis of sample number 95 using the DNA chip of the invention.

Figure 4J:
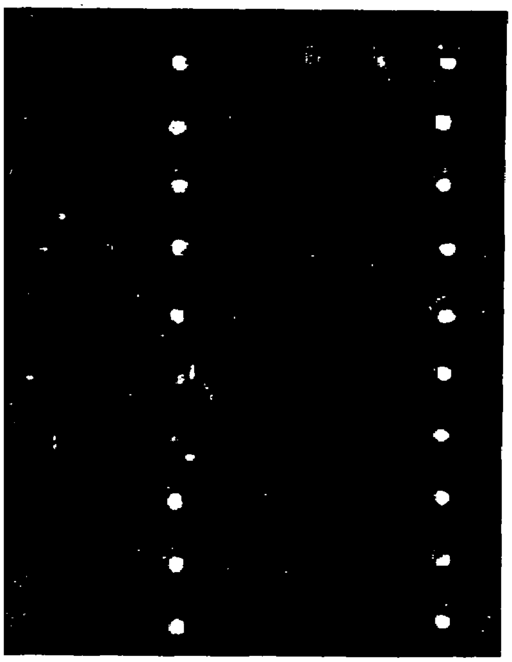

FIG. 4*j* is a photograph showing the result of DNA analysis of sample number 107 using the DNA chip of the invention.

Figure 4K:
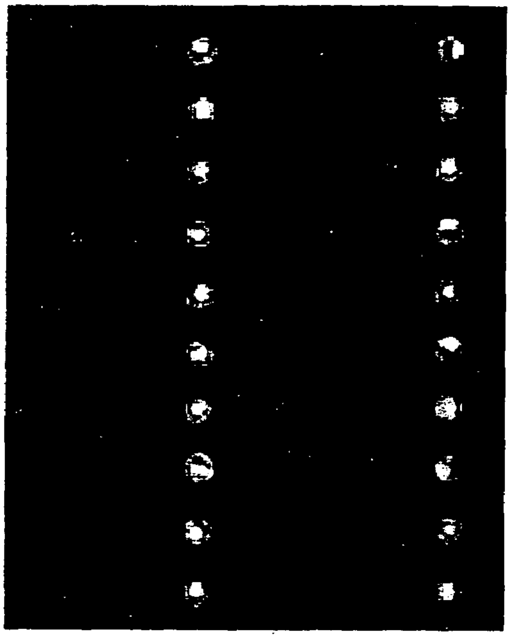

FIG. 4*k* is a photograph showing the result of DNA analysis of sample number 115 using the DNA chip of the invention.

Figure 4L:
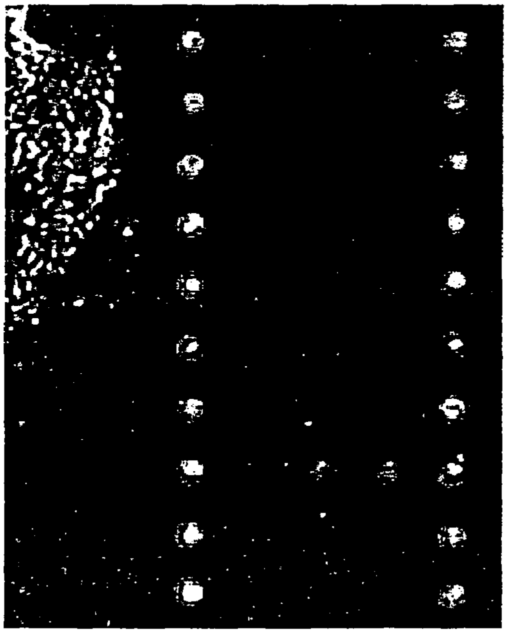

FIG. 4*l* is a photograph showing the result of DNA analysis of sample number 124 using the DNA chip of the invention.

DETAILED DESCRIPTION OF THE INVENTION

The genotyping kit of the invention for diagnosis of human papillomavirus (HPV) infection comprises: a DNA chip with probes that have nucleotide sequences complementary to DNA of HPV; primers for amplifying DNA obtained from clinical samples by PCR; and, means for labeling amplified DNA hybridized with the probes of the said DNA chip. The DNA chip may further comprise position markers to locate probes, and staining or labeling is performed by using means for labeling comprising preferably biotin-binding material, most preferably, streptavidin-R-phycoerythrin which is a conjugate of a fluorophore and a protein with biotin-binding sites.

The process for preparing DNA chip contained in the said HPV genotyping kit comprises the steps of: preparing 5' terminal amine-linked DNA probes which have nucleotide sequences complementary to DNA of HPV; affixing the DNA probes thus prepared to an aldehyde-derivatized solid surface; and, reducing excessive aldehydes not reacted with amine.

The process for preparing DNA chip of the invention is described in more detail by the following steps.

Step 1: Preparation of Probes

5' terminal amine-linked DNA probes that have nucleotide sequences complementary to the DNA of HPV are prepared: The nucleotide sequences of the probes are designed and synthesized to have nucleotide sequences complementary to the DNA of HPV, preferably the L1 region of HPV DNA, and the probes are prepared by linking amine group at 5' terminal of the nucleotide sequences which enables the probes to bind to aldehyde-derivatized solid surface.

Step 2: Affixture of Probes

DNA probes prepared in Step 1 are affixed to an aldehyde-derivatized surface of a solid support, preferably glass. The probes are affixed to the surface of solid support via Schiff's base reaction between an aldehyde group on the surface of solid support and an amine group at 5' terminal of the probe under an environment of 30 to 40° C. and 70 to 100% humidity, while controlling the concentration of probes in a range of preferably 100 to 300 μmol/μl, more preferably 200 μmol/μl.

Step 3: Preparation of DNA Chip

Excessive aldehydes not reacted with amine on the solid surface are reduced by employing a reducing agent of NaBH (sodium borohydride), finally to prepare DNA chip.

The method for diagnosis of HPV infection using HPV genotyping kit of the invention comprises the steps of: amplifying DNA obtained from clinical samples by PCR with primers of the HPV genotyping kit; applying the amplified DNA to the DNA chip to hybridize the amplified DNA with DNA probes of the DNA chip; and, detecting DNA bound on the surface of the DNA chip after labeling hybridized DNA.

The method for diagnosis of HPV infection using HPV genotyping kit of the invention is further illustrated by the following steps.

Step 1: Amplification of Sample DNA

DNA obtained from clinical samples is amplified using the primers of HPV genotyping kit, where polymerase chain reaction (PCR) employing biotin-16-dUTP is carried out to give biotin-containing amplified DNA.

Step 2: Hybridization

Amplified DNA thus obtained is applied to the DNA chip of HPV genotyping kit and hybridized with the probes of the DNA chip.

Step 3: Detection

The amplified sample DNA hybridized with the probes are labeled with means for labeling and detected with a confocal laser scanner: Streptavidin-R-phycoerythrin is preferably used as means for labeling which is a conjugate of a fluorophore with a high extinction coefficient and a protein with 4 biotin-binding sites, which enables high sensitivity detection of hybridized spots on the DNA chip by the confocal laser scanner.

HPV genotyping kit of the invention is an implement that can detect HPV infection in a simple and accurate manner, as well as identify the types of infecting HPV, therefore, it may contribute to early diagnosis, prevention and treatment of cervical cancer.

The present invention is further illustrated in the following examples, which should not be taken to limit the scope of the invention. Particularly, though DNA chip with 19 probes was prepared in the Examples described below, it is to be understood that the present invention is not limited by types and numbers of probes, but DNA chips using nucleotide sequences derived from HPV DNA and any variety of detection kits using the said DNA chips are intended to be included within the scope of the invention.

EXAMPLE 1

Preparation of DNA Chip

Prevalent HPV types including 13 high-risk types (HPV type 16, 18, 31, 33, 35, 39, 45, 51, 52, 56, 58, 59, 66) and 6 low-risk types (HPV type 6, 11, 34, 40, 42, 44) were selected, and genotype-specific probe for each HPV type possessing amine group at 5' terminal of the sequence was prepared for the detection of HPV genotypes. The nucleotide sequence of each probe is as follows:

HPV 16: 5'-gtcattatgtgctgccatatctacttcaga-3' (SEQ ID NO: 1),

HPV 18: 5'-tgcttctacacagtctcctgtacctgggca-3' (SEQ ID NO: 2),

HPV 31: 5'-tgtttgtgctgcaattgcaaacagtgatac-3' (SEQ ID NO: 3),

HPV 33: 5'-tttatgcacacaagtaactagtgacagtac-3' (SEQ ID NO: 4),

HPV 35: 5'-gtctgtgtgttctgctgtgtcttctagtga-3' (SEQ ID NO: 5),

HPV 39: 5'-tctacctctatagagtcttccataccttct-3' (SEQ ID NO: 6),

HPV 45: 5'-acacaaaatcctgtgccaagtacatatgac-3' (SEQ ID NO: 7),

HPV 51: 5'-agcactgccactgctgcggtttccccaaca-3' (SEQ ID NO: 8),

HPV 52: 5'-tgctgaggttaaaaaggaaagcacatataa-3' (SEQ ID NO: 9),

HPV 56: 5'-gtactgctacagaacagttaagtaaatatg-3' (SEQ ID NO: 10),

HPV 58: 5'-attatgcactgaagtaactaaggaaggtac-3' (SEQ ID NO: 11),

HPV 59: 5'-ctgtgtgtgcttctactactgcttctattc-3' (SEQ ID NO: 12),

HPV 66: 5'-ctattaatgcagctaaaagcacattaacta-3' (SEQ ID NO: 13),

HPV 6: 5'-atccgtaactacatcttccacatacaccaa-3' (SEQ ID NO: 14),

HPV 11: 5'-atctgtgtctaaatctgctacatacactaa-3' (SEQ ID NO: 15),

HPV 34: 5'-tacacaatccacaagtacaaatgcaccata-3' (SEQ ID NO: 16),

HPV 40: 5'-gctgccacacagtcccccacaccaacccca-3' (SEQ ID NO: 17),

HPV 42: 5'-ctgcaacatctggtgatacatatacagctg-3' (SEQ ID NO: 18),

HPV 44: 5'-gccactacacagtcccctccgtctacatat-3' (SEQ ID NO: 19),

DNA chip was prepared as follows: each probe prepared above was dissolved in 3×SSC (45 mM sodium citrate, 0.45M NaCl, pH 7.0) at a concentration of 200 μmol/μl, and spotted onto an aldehyde-derivatized silylated slide (CSS-100, CEL, Houston, Tex., USA) to form an array of spots with size of 150 μm at 300 μm spacing between spots using a microarrayer (GMS 417 Arrayer, TakaRa, Japan), followed by performing Schiff's base reaction under an environment of 37° C. and over 70% humidity for 4 hours. The slide was washed with 0.2% (w/v) sodium dodecyl sulfate (SDS), and with triple distilled water. Then, the slide was treated with NaBH solution (0.1 g $NaBH_4$, 30 ml phosphate buffered saline (PBS), 10 ml ethanol) for 5 minutes to reduce excessive aldehydes not reacted with amine, followed by washing with triple distilled water and air-drying.

EXAMPLE 2

Preparation of Samples

In order to detect HPV infection in human cervical swabs, DNA was extracted from the said specimen and then purified. To test the adequacy of sample DNA, the said purified DNA was PCR amplified with beta-globin primers, PC03(5'-acacaactgtgttcactagc-3', SEQ ID NO: 20) and 5'-biotin linked-PC04(5'-caacttcatccacgttcacc-3', SEQ ID NO: 21). The DNA samples which reveal beta-globin DNA amplification were selected and used for further analyses of HPV DNA.

As HPV DNA standards, plasmid DNA comprising HPV sequence obtained from the following distributors were used: HPV types 6, 11, 40, 45, and 51 from Dr. Ethel-Michele de Villiers, Angewandte Tumorvirologie, Deutsches Krebsforschungszentrum, Im Neuenheimer Feld 242, 69009 Heidelerg, Germany; HPV types 35, 44, and 56 from Dr. Attila Lörincz, Vice President, R&D and Scientific Director, Digene Diagnostics, Inc., 2301-B Broadbirch Drive, Silver Spring, Md. 20904, USA; HPV types 42, 58, and 59 from Dr. Toshihiko Matsukura, Department of Pathology and Laboratory of Pathology, AIDS Research Center, National Institute of Infectious Disease, Tokyo 162, Japan; HPV types 33, 34, 39, 52, and 66 from Dr. Gérard Orth, Unité Mixte Institut Pasteur/INSERM (U. 190), Institut Pasteur, 25 rue du Docteur Roux, 75724 Paris Cedex 15, France.

Additionally, DNA extracted and purified from following cell lines were used as positive controls: SiHa cell line (HPV 16, KCLB 30035, Human squamous carcinoma, cervix) and HeLa cell line (HPV 18, KCLB 10002, Human eplthelial carcinoma, cervix) which were purchased from Korean Cell Line Bank (Seoul National University, College of Medicine, Seoul, Korea).

Selected sample DNA described above were PCR amplified using the following primer sets: $GP5^+$ (5'-tttgttactgtggtagatactac-3', SEQ ID NO: 22) and biotin-linked $GP6^-$, Bio-$GP6^+$ (5'-Biotin-gaaaaataaactgtaaatcatattc-3', SEQ ID NO: 23), and, $GP5d^+$ (5'-tttkttachgtkgtdgatacyac-3', SEQ ID NO: 24) and $GP6d^+$ (5'-gaaahataaaytgyaadtcataytc-3', SEQ ID NO: 25). The modified primer set $GP5d^+$/$GP6d^+$ was developed to facilitate PCR amplification of HPV DNA from clinical samples. In describing the nucleotide sequence, 'k' is employed to mean 'g' or 't', 'h' is 't', 'a', or 'c', 'd' is 'a', 't', or 'g', and 'y' is 't' or 'c'.

EXAMPLE 2-1

Preparation of Positive Control Samples

To obtain biotin-labeled amplified DNA samples, HPV 16 and HPV 18 DNA purified above were amplified by PCR with primers, $GP5^+$ and Bio-$GP6^+$. PCR was performed in a 50 μl of reaction mixture containing PCR buffer (50 mM KCl, 4 mM $MgCl_2$, 10 mM Tris-HCl, pH 8.3), 0.1 μg of DNA, 4.5 mM $MgCl_2$, 50 μmol of each primer, 40 μM each of dATP, dCTP, dGTP (Pharmacia), 30 μM of dTTP (Pharmacia), 10 μM biotin-16-dUTP (Boehringer Manheim, Germany) and 1 unit of Taq polymerase (TaKaRa, Japan) with 40 cycles of denaturation for 1 min at 94° C., primer annealing for 2 min at 40° C., and extension for 1 min 30 sec at 72° C.

EXAMPLE 2-2

Preparation of HPV Standards

Biotin-linked amplified HPV DNA samples were prepared anologously as in Example 2-1, except for employing templates of various HPV plasmids described above.

EXAMPLE 2-3

Preparation of Sample DNA from Clinical Samples

Biotin-linked amplified DNA samples were obtained analogously as in Example 2-1, except that DNA obtained from uterine cervical swabs were used as templates, GP5d and GP6d$^-$ were employed as primers, and PCR was performed with 40 cycles of denaturation for 1 min at 94° C., primer annealing for 2 min at 55° C., and extension for 1 min 30 sec at 72° C.

EXAMPLE 3

Detection of HPV Infection Using DNA Chip

Amplified DNA samples obtained in Example 2 were applied to the DNA chip prepared in Example 1, and hybridization was carried out in a hybridization reaction chamber made up of the Cover slip (GRACE Bio-Labs, USA, PC4L-1.0) with 100 μl capacity.

Figure 1:
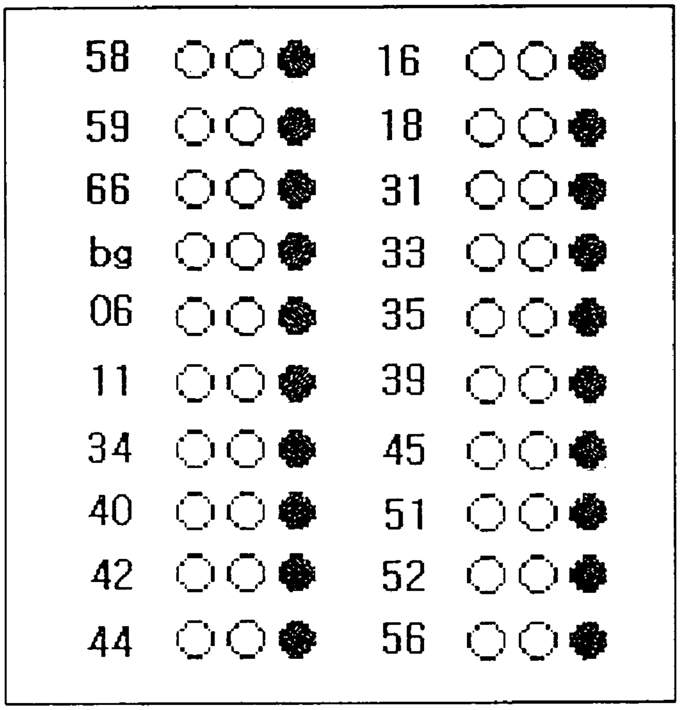
FIG. 1 is a schematic representation of the types and positions of the probes on the DNA chip.

As for the quantity of hybridization reaction samples, 10 μl each of amplified product was used for positive controls and plasmid DNA, and a mixture of 10 μl of HPV amplified product and 5 μl of beta-globin amplified product was used for DNA obtained from cervical swabs. The said reaction samples were denatured by adding 3N NaOH solution (10% v/v) and standing for 5 min at room temperature, and neutralized by adding 1 M Tris-HCl (pH 7.2, 5% v/v) followed by 3N HCl (10% v/v) and cooling for 5 min on ice. The samples were then mixed with a hybridization solution made up of 6×SSPE (saline-sodium phosphate-EDTA buffer, Sigma Chemical Co., St. Louis, Mo., USA) and 0.2% SDS (sodium dodecyl sulfate), and applied onto the DNA chip. Hybridization reaction was carried out for 2 hours at 40° C., followed by washing with 3×SSPE for 2 min, 1×SSPE for 2 min, and air-drying at room temperature. The DNA chip hybridized with sample DNA was stained with a mixture of 5 μl of streptavidin-R-phycoerythrin conjugate (50 μg/ml) and 95 μl of 3×SSPE for 25 min, washed with 1×SSPE, and then analyzed for fluorescent signals (extinction 480 nm, emission >520 nm) by using a confocal laser scanner (GMS 418 Array Scanner, TaKaRa, Japan) (see: FIG. 1, FIGS. 2*a*-2*m*, 3*a*-3*f*, and 4*a*-4*l*). FIG. 1 is a schematic representation of the type and position of the probes on DNA chip: each number indicates each HPV probe, 'bg' indicates beta-globin probe placed to verify proper performance of hybridization reaction, 'M' indicates position marker for locating probes, open circles (○) indicate HPV and beta-globin probe-affixed positions, and closed circles (●) indicate positions of 'M'. FIGS. 2*a*-2*m* are photographs showing the results of high-risk group HPV DNA analyses using HPV plasmids and cervical cancer cell lines: FIG. 2*a* is a photograph showing the result of HPV 16 DNA analysis, FIG. 2*b*, the result of HPV 18 DNA analysis, FIG. 2*c*, the result of HPV 31 DNA analysis, FIG. 2*d*, the result of HPV 33 DNA analysis, FIG. 2*e*, the result of HPV 35 DNA analysis, FIG. 2*f*, the result of HPV 39 DNA analysis, FIG. 2*g*, the result of HPV 45 DNA analysis, FIG. 2*h*, the result of HPV 51 DNA analysis, FIG. 2I, the result of HPV 52 DNA analysis, FIG. 2*j*, the result of HPV 56 DNA analysis, FIG. 2*k*, the result of HPV 58 DNA analysis, FIG. 21, the result of HPV 59 DNA analysis, and FIG. 2*m*, the result of HPV 66 DNA analysis. FIGS. 3*a*-3*f* are photographs showing the results of low-risk group HPV DNA analyses using HPV plasmids: FIG. 3*a* is a photograph showing the results of HPV 6 DNA analysis, FIG. 3*b* is a photograph showing the result of HPV 11 DNA analysis, FIG. 3*c*, the result of HPV 34 DNA analysis, FIG. 3*d*, the result of HPV 40 DNA analysis, FIG. 3*e*, the result of HPV 42 DNA analysis, and FIG. 3*f*, the result of HPV 44 DNA analysis. As shown in FIGS. 2*a*-2*m* and FIGS. 3*a*-3*f*, hybridization signals produced by the amplified DNA of HPV plasmid standards and HPV positive controls (cervical cancer cell lines) were observed clearly on the corresponding probes without significant cross-hybridization.

EXAMPLE 4

Detection of HPV Infection in Clinical Samples Using DNA Chip

In order to examine the accuracy and efficiency of diagnosis by the DNA chip of the invention, clinical samples were PCR amplified with primers comprising nucleotide sequences set forth in SEQ ID NO: 20-25, and then, for proper samples, diagnostic procedure using the DNA chip was performed to detect HPV infection as well as to determine the type of the infection.

DNA isolated from 124 specimens from uterine cervix were amplified using the method described in Example 2-3, and analyzed for HPV infection by using the DNA chip of the invention as described in Example 3. The above 124 isolated DNA were subjected to PCR-RFLP (Restriction Fragment Length Polymorphism) assay in which DNA was amplified, treated with restriction enzyme Ava II, Afa I, Bgl II, Acc I or Ava I, and then the pattern of fragmentation produced by the restriction enzymes was analyzed to determine 6 types of HPV infection (HPV 16, 18, 31, 33, 52 and 58). The results of PCR-RFLP were confirmed by employing type-specific PCR technique (see: Hwang, T., J. Kor. Med. Sci., 15:593-599, 1999; Fujinaga, Y. et al., J. General Virology, 72:1039-1044, 1991). The results of the two methods, DNA chip of the invention and PCR-RFLP followed by type-specific PCR, were compared to determine diagnostic efficiency of the DNA chip method (see: FIGS. 4*a*-4*l*, Table 1). FIGS. 4*a*-4*l* are photographs showing Examples of the results of DNA chip analyses of cervical swab specimens for HPV infection. As shown in FIGS. 4*a*-4*l*, detailed diagnoses of HPV infection in the clinical samples via accurate detection and genotyping of the infecting HPV were successfully accomplished by using the DNA chip of the invention. The degree of agreement of the two methods was also measured for the above 124 cases of clinical specimens (see: Table 1).

TABLE 1

Comparison of the detection/genotyping results obtained by the invented genotyping kit and PCR-RFLP assay of prior art

| Sample Nos. | Detection/Genotyping by Genotyping Kit | Detection/Genotyping by PCR-RFLP Assay |
|---|---|---|
| 34 | — | — |
| 35 | — | — |
| 36 | — | HPV 16 |
| 37 | HPV 16, 56 | HPV 16 |
| 38 | HPV 58 | HPV 58 |
| 39 | HPV 56, 58 | HPV 33 |
| 40 | HPV 16 | HPV 16 |
| 41 | HPV 16 | HPV 18 |
| 42 | HPV 16 | HPV 16 |
| 43 | HPV 16 | HPV 16 |
| 46 | HPV 16 | HPV 16 |
| 47 | HPV 16 | HPV 16 |
| 48 | HPV 33 | HPV 33 |
| 49 | HPV 33 | HPV 33 |
| 50 | HPV 51 | HPV 18 |
| 51 | HPV 16 | HPV 16 |
| 52 | HPV 33 | HPV 33 |
| 53 | HPV 58 | HPV 58 |
| 54 | HPV 16, 18 | HPV 16, 18 |
| 57 | HPV 58 | HPV 58 |
| 58 | HPV 33 | HPV 33 |
| 59 | HPV 18 | HPV 18 |
| 60 | HPV 18 | HPV 18 |
| 62 | HPV 39 | — |
| 63 | HPV 35 | HPV 35 |
| 64 | — | — |
| 65 | HPV 58 | HPV 58 |
| 66 | — | — |
| 68 | No typing | HPV 52, 58 |
| 69 | No typing | — |
| 70 | HPV 16 | HPV 16 |
| 71 | HPV 16 | HPV 16 |
| 72 | — | — |
| 73 | HPV 16 | HPV 16 |
| 75 | — | HPV 16 |
| 76 | HPV 16 | HPV 16 |
| 77 | HPV 18 | HPV 16 |
| 78 | HPV 16 | HPV 16 |
| 79 | HPV 33, 35 | HPV 33 |
| 80 | HPV 33 | HPV 33 |
| 81 | HPV 16 | HPV 16 |
| 82 | HPV 16 | HPV 16 |
| 83 | — | HPV 33 |
| 84 | HPV 16 | HPV 16 |
| 85 | HPV 16 | HPV 16 |
| 86 | HPV 16 | HPV 16 |
| 87 | HPV 16 | HPV 16 |
| 88 | HPV 16 | HPV 16 |
| 89 | HPV 58 | HPV 58 |
| 90 | HPV 16 | HPV 16 |
| 91 | HPV 16 | HPV 16 |
| 92 | HPV 16 | HPV 16 |
| 93 | HPV 16 | HPV 16 |
| 94 | HPV 16 | HPV 16 |
| 95 | HPV 16 | HPV 16 |
| 96 | — | HPV 33 |
| 97 | HPV 16 | HPV 16 |
| 98 | HPV 16 | HPV 16 |
| 99 | HPV 16 | HPV 16 |
| 100 | HPV 16 | HPV 16 |
| 101 | HPV 16 | HPV 16 |
| 102 | HPV 16 | HPV 16 |
| 103 | HPV 16 | HPV 16 |
| 104 | HPV 16 | HPV 16 |
| 105 | HPV 16 | HPV 16 |
| 106 | HPV 16 | HPV 16 |
| 107 | HPV 16 | HPV 16 |
| 108 | HPV 16 | HPV 16 |
| 109 | HPV 16 | HPV 16 |
| 110 | HPV 16 | HPV 16 |
| 111 | HPV 18 | HPV 18 |
| 112 | HPV 16 | HPV 16 |

TABLE 1-continued

Comparison of the detection/genotyping results obtained by the invented genotyping kit and PCR-RFLP assay of prior art

| Sample Nos. | Detection/Genotyping by Genotyping Kit | Detection/Genotyping by PCR-RFLP Assay |
|---|---|---|
| 113 | HPV 16 | HPV 16 |
| 114 | HPV 16 | HPV 16 |
| 115 | HPV 31, 35 | HPV 31 |
| 116 | HPV 16 | HPV 16 |
| 117 | HPV 16 | HPV 16 |
| 118 | HPV 16 | HPV 16 |
| 119 | HPV 16 | HPV 16 |
| 120 | HPV 16 | HPV 16 |
| 121 | HPV 16 | HPV 16 |
| 123 | HPV 16 | HPV 16 |
| 124 | HPV 51 | HPV 31 |

In Table 1, "no typing" indicates presence of HPV DNA after PCR amplification with HPV type undetermined by the specific method, and "–" indicates absence of HPV DNA after PCR amplification. As shown in Table 1, the results obtained by two methods under comparison were in a good accordance demonstrating the reliability of DNA chip analysis. Considering the simplicity and rapidity of procedure, together with convenient detection of diverse genotypes and multiple infection, DNA chip analysis is thought to be by far more advantageous than PCR-RFLP followed by type-specific PCR and other related methods. The accuracy of diagnosis by the DNA chip of the invention was calculated to be 96.5% and the reproducibility was 95% based on the above 124 cases, which are considered to be the subject of improvement upon completion of larger size case studies in progress. The FDA (Food and Drug Administration) approved Hybrid Capture kit increasingly employed recently for fast diagnosis of HPV infection was reported to have 98% accuracy in detecting and distinguishing high- or low-risk HPV infection. DNA chip analysis has a competitive efficiency and an additional advantage of genotyping when compared with the Hybrid Capture assay. The above information indicates that diagnosis of HPV infection using the genotyping kit of the invention is superior in many aspects to the conventional methods employed for the same purpose.

As clearly illustrated and demonstrated as aboves, the present invention provides a genotyping kit for identifying genotypes of HPV from clinical samples of infected patients and a method for diagnosis of HPV infection by genotyping the infecting virus using the said genotyping kit. The HPV genotyping kit of the invention comprises: a DNA chip with probes that have nucleotide sequences complementary to DNA of HPV; primers for amplifying DNA obtained from clinical samples by PCR; and, means for labeling amplified DNA hybridized with the probes of the said DNA chip. The method for diagnosis of HPV infection using the said HPV genotyping kit comprises the steps of: amplifying DNA obtained from clinical samples by PCR with primers of the kit; applying the amplified DNA to DNA chip to hybridize the amplified DNA with the probes of the DNA chip; and, detecting DNA bound on the surface of the DNA chip after labeling DNA hybridized with the probes of the DNA chip with means of labeling of the HPV genotyping kit. HPV genotyping kit of the invention is an implement that can detect HPV infection in a simple and accurate manner, as well as identify the types of infecting HPV, therefore, it may contribute to early diagnosis, prevention and treatment of cervical cancer.

Various modifications of the invention in addition to those shown and described herein will be apparent to those skilled in the art from the foregoing descriptions. Such modifications are also intended to fall within the scope of the appended claims.

What is claimed is:

1. A method for diagnosis of the genotype of Human Papillomavirus (HPV) infection comprising:

(a) amplifying DNA obtained from clinical samples to obtain biotin-containing amplified DNA using a kit comprising:

(i) a DNA chip comprising a combination of each of the genotype specific HPV nucleic acid sequence probes set forth as:

SEQ ID NO: 1 or the fully complementary sequence thereof, specific for HPV genotype HPV-16;

SEQ ID NO: 2 or the fully complementary sequence thereof, specific for HPV genotype HPV-18;

SEQ ID NO: 3 or the fully complementary sequence thereof, specific for HPV genotype HPV-31;

SEQ ID NO: 4 or the fully complementary sequence thereof, specific for HPV genotype HPV-33;

SEQ ID NO: 5 or the fully complementary sequence thereof, specific for HPV genotype HPV-35;

SEQ ID NO: 6 or the fully complementary sequence thereof, specific for HPV genotype HPV-39;

SEQ ID NO: 7 or the fully complementary sequence thereof, specific for HPV genotype HPV-45;

SEQ ID NO: 8 or the fully complementary sequence thereof, specific for HPV genotype HPV-51;

SEQ ID NO: 9 or the fully complementary sequence thereof, specific for HPV genotype HPV-52;

SEQ ID NO: 10 or the fully complementary sequence thereof, specific for HPV genotype HPV-56;

SEQ ID NO: 11 or the fully complementary sequence thereof, specific for HPV genotype HPV-58;

SEQ ID NO: 12 or the fully complementary sequence thereof, specific for HPV genotype HPV-59;

SEQ ID NO: 13 or the fully complementary sequence thereof, specific for HPV genotype HPV-66;

SEQ ID NO: 14 or the fully complementary sequence thereof, specific for HPV genotype HPV-6;

SEQ ID NO: 15 or the fully complementary sequence thereof, specific for HPV genotype HPV-11;

SEQ ID NO: 16 or the fully complementary sequence thereof, specific for HPV genotype HPV-34;

SEQ ID NO: 17 or the fully complementary sequence thereof, specific for HPV genotype HPV-40;

SEQ ID NO: 18 or the fully complementary sequence thereof, specific for HPV genotype HPV-42; and SEQ ID NO: 19 or the fully complementary sequence thereof, specific for HPV genotype HPV-44, and a glass slide to which the probes are attached;

(ii) biotin-labeled primers for amplifying DNA obtained from clinical samples; and (iii) means for labeling amplified DNA that hybridizes with the probes of the DNA chip;

(b) applying the amplified DNA to the DNA chip under conditions which allow hybridization of the amplified DNA to the probes;

(c) applying a biotin-binding label to the hybridized DNA on the chip; and (d) detecting hybridized DNA on the surface of the DNA chip at a position corresponding to the location of a genotype specific HPV probe by detecting the biotin-binding label, wherein detection of the biotin-binding label indicates the presence of HPV DNA in the sample which corresponds to the genotype of the HPV probe to which the DNA is hybridized.

2. A method for diagnosis of the genotype of Human Papillomavirus (HPV) infection comprising:

(a) amplifying DNA obtained from clinical samples to obtain amplified DNA containing a first label using a kit comprising:

(i) a DNA chip comprising a combination of each of the genotype specific HPV nucleic acid sequence probes set forth as:

SEQ ID NO: 1 or the fully complementary sequence thereof, specific for HPV genotype HPV-16;

SEQ ID NO: 2 or the fully complementary sequence thereof, specific for HPV genotype HPV-18;

SEQ ID NO: 3 or the fully complementary sequence thereof, specific for HPV genotype HPV-31;

SEQ ID NO: 4 or the fully complementary sequence thereof, specific for HPV genotype HPV-33;

SEQ ID NO: 5 or the fully complementary sequence thereof, specific for HPV genotype HPV-35;

SEQ ID NO: 6 or the fully complementary sequence thereof, specific for HPV genotype HPV-39;

SEQ ID NO: 7 or the fully complementary sequence thereof, specific for HPV genotype HPV-45;

SEQ ID NO: 8 or the fully complementary sequence thereof, specific for HPV genotype HPV-51;

SEQ ID NO: 9 or the fully complementary sequence thereof, specific for HPV genotype HPV-52;

SEQ ID NO: 10 or the fully complementary sequence thereof, specific for HPV genotype HPV-56;

SEQ ID NO: 11 or the fully complementary sequence thereof, specific for HPV genotype HPV-58;

SEQ ID NO: 12 or the fully complementary sequence thereof, specific for HPV genotype HPV-59;

SEQ ID NO: 13 or the fully complementary sequence thereof, specific for HPV genotype HPV-66;

SEQ ID NO: 14 or the fully complementary sequence thereof, specific for HPV genotype HPV-6;

SEQ ID NO: 15 or the fully complementary sequence thereof, specific for HPV genotype HPV-11;

SEQ ID NO: 16 or the fully complementary sequence thereof, specific for HPV genotype HPV-34;

SEQ ID NO: 17 or the fully complementary sequence thereof, specific for HPV genotype HPV-40;

SEQ ID NO: 18 or the fully complementary sequence thereof, specific for HPV genotype HPV-42; and SEQ ID NO: 19 or the fully complementary sequence thereof, specific for HPV genotype HPV-44, and a glass slide to which the probes are attached;

(ii) primers containing the first label for amplifying DNA obtained from clinical samples; and (iii) means for labeling amplified DNA with a second label, wherein the DNA hybridizes with the probes of the DNA chip;

(b) applying the amplified DNA to the DNA chip under conditions which allow hybridization of the amplified DNA to the probes;

(c) applying the second label to the hybridized DNA on the chip, wherein the second label binds to the first label; and (d) detecting hybridized DNA on the surface of the DNA chip at a position corresponding to the location of a genotype specific HPV probe by detecting the second label, wherein detection of the second label indicates the presence of HPV DNA in the sample which corresponds to the genotype of the HPV probe to which the DNA is hybridized.

* * * * *

```
                              SEQUENCE LISTING

<160> NUMBER OF SEQ ID NOS: 25

<210> SEQ ID NO 1
<211> LENGTH: 30
<212> TYPE: DNA
<213> ORGANISM: Artificial Sequence
<220> FEATURE:
<223> OTHER INFORMATION: primer HPV16

<400> SEQUENCE: 1

gtcattatgt gctgccatat ctacttcaga                                    30


<210> SEQ ID NO 2
<211> LENGTH: 30
<212> TYPE: DNA
<213> ORGANISM: Artificial Sequence
<220> FEATURE:
<223> OTHER INFORMATION: primer HPV18

<400> SEQUENCE: 2

tgcttctaca cagtctcctg tacctgggca                                    30


<210> SEQ ID NO 3
<211> LENGTH: 30
<212> TYPE: DNA
<213> ORGANISM: Artificial Sequence
<220> FEATURE:
<223> OTHER INFORMATION: primer HPV31

<400> SEQUENCE: 3

tgtttgtgct gcaattgcaa acagtgatac                                    30


<210> SEQ ID NO 4
<211> LENGTH: 30
<212> TYPE: DNA
<213> ORGANISM: Artificial Sequence
<220> FEATURE:
<223> OTHER INFORMATION: primer HPV33

<400> SEQUENCE: 4

tttatgcaca caagtaacta gtgacagtac                                    30


<210> SEQ ID NO 5
<211> LENGTH: 30
<212> TYPE: DNA
<213> ORGANISM: Artificial Sequence
<220> FEATURE:
<223> OTHER INFORMATION: primer HPV35

<400> SEQUENCE: 5

gtctgtgtgt tctgctgtgt cttctagtga                                    30


<210> SEQ ID NO 6
<211> LENGTH: 30
<212> TYPE: DNA
<213> ORGANISM: Artificial Sequence
<220> FEATURE:
<223> OTHER INFORMATION: primer HPV39
```

-continued

<400> SEQUENCE: 6
tctacctcta tagagtcttc cataccttct 30

<210> SEQ ID NO 7
<211> LENGTH: 30
<212> TYPE: DNA
<213> ORGANISM: Artificial Sequence
<220> FEATURE:
<223> OTHER INFORMATION: primer HPV45

<400> SEQUENCE: 7
acacaaaatc ctgtgccaag tacatatgac 30

<210> SEQ ID NO 8
<211> LENGTH: 30
<212> TYPE: DNA
<213> ORGANISM: Artificial Sequence
<220> FEATURE:
<223> OTHER INFORMATION: primer HPV51

<400> SEQUENCE: 8
agcactgcca ctgctgcggt ttccccaaca 30

<210> SEQ ID NO 9
<211> LENGTH: 30
<212> TYPE: DNA
<213> ORGANISM: Artificial Sequence
<220> FEATURE:
<223> OTHER INFORMATION: primer HPV52

<400> SEQUENCE: 9
tgctgaggtt aaaaaggaaa gcacatataa 30

<210> SEQ ID NO 10
<211> LENGTH: 30
<212> TYPE: DNA
<213> ORGANISM: Artificial Sequence
<220> FEATURE:
<223> OTHER INFORMATION: primer HPV56

<400> SEQUENCE: 10
gtactgctac agaacagtta agtaaatatg 30

<210> SEQ ID NO 11
<211> LENGTH: 30
<212> TYPE: DNA
<213> ORGANISM: Artificial Sequence
<220> FEATURE:
<223> OTHER INFORMATION: primer HPV58

<400> SEQUENCE: 11
attatgcact gaagtaacta aggaaggtac 30

<210> SEQ ID NO 12
<211> LENGTH: 30
<212> TYPE: DNA
<213> ORGANISM: Artificial Sequence
<220> FEATURE:
<223> OTHER INFORMATION: primer HPV59

<400> SEQUENCE: 12
ctgtgtgtgc ttctactact gcttctattc 30

<210> SEQ ID NO 13
<211> LENGTH: 30

-continued

<212> TYPE: DNA
<213> ORGANISM: Artificial Sequence
<220> FEATURE:
<223> OTHER INFORMATION: primer HPV66

<400> SEQUENCE: 13
ctattaatgc agctaaaagc acattaacta 30

<210> SEQ ID NO 14
<211> LENGTH: 30
<212> TYPE: DNA
<213> ORGANISM: Artificial Sequence
<220> FEATURE:
<223> OTHER INFORMATION: primer HPV6

<400> SEQUENCE: 14
atccgtaact acatcttcca catacaccaa 30

<210> SEQ ID NO 15
<211> LENGTH: 30
<212> TYPE: DNA
<213> ORGANISM: Artificial Sequence
<220> FEATURE:
<223> OTHER INFORMATION: primer HPV11

<400> SEQUENCE: 15
atctgtgtct aaatctgcta catacactaa 30

<210> SEQ ID NO 16
<211> LENGTH: 30
<212> TYPE: DNA
<213> ORGANISM: Artificial Sequence
<220> FEATURE:
<223> OTHER INFORMATION: primer HPV34

<400> SEQUENCE: 16
tacacaatcc acaagtacaa atgcaccata 30

<210> SEQ ID NO 17
<211> LENGTH: 30
<212> TYPE: DNA
<213> ORGANISM: Artificial Sequence
<220> FEATURE:
<223> OTHER INFORMATION: primer HPV40

<400> SEQUENCE: 17
gctgccacac agtcccccac accaacccca 30

<210> SEQ ID NO 18
<211> LENGTH: 30
<212> TYPE: DNA
<213> ORGANISM: Artificial Sequence
<220> FEATURE:
<223> OTHER INFORMATION: primer HPV42

<400> SEQUENCE: 18
ctgcaacatc tggtgataca tatacagctg 30

<210> SEQ ID NO 19
<211> LENGTH: 30
<212> TYPE: DNA
<213> ORGANISM: Artificial Sequence
<220> FEATURE:
<223> OTHER INFORMATION: primer HPV44

<400> SEQUENCE: 19

-continued gccactacac agtcccctcc gtctacatat 30

<210> SEQ ID NO 20
<211> LENGTH: 20
<212> TYPE: DNA
<213> ORGANISM: Artificial Sequence
<220> FEATURE:
<223> OTHER INFORMATION: primer PC03

<400> SEQUENCE: 20
acacaactgt gttcactagc 20

<210> SEQ ID NO 21
<211> LENGTH: 20
<212> TYPE: DNA
<213> ORGANISM: Artificial Sequence
<220> FEATURE:
<223> OTHER INFORMATION: primer PC04

<400> SEQUENCE: 21
caacttcatc cacgttcacc 20

<210> SEQ ID NO 22
<211> LENGTH: 23
<212> TYPE: DNA
<213> ORGANISM: Artificial Sequence
<220> FEATURE:
<223> OTHER INFORMATION: primer GP5+

<400> SEQUENCE: 22
tttgttactg tggtagatac tac 23

<210> SEQ ID NO 23
<211> LENGTH: 25
<212> TYPE: DNA
<213> ORGANISM: Artificial Sequence
<220> FEATURE:
<223> OTHER INFORMATION: primer GP6+

<400> SEQUENCE: 23
gaaaaataaa ctgtaaatca tattc 25

<210> SEQ ID NO 24
<211> LENGTH: 23
<212> TYPE: DNA
<213> ORGANISM: Artificial Sequence
<220> FEATURE:
<223> OTHER INFORMATION: primer GP5d+

<400> SEQUENCE: 24
tttkttachg tkgtdgatac yac 23

<210> SEQ ID NO 25
<211> LENGTH: 25
<212> TYPE: DNA
<213> ORGANISM: Artificial Sequence
<220> FEATURE:
<223> OTHER INFORMATION: primer GP6d+

<400> SEQUENCE: 25
gaaahataaa ytgyaadtca taytc 25